(12) United States Patent
O'Connor et al.

(10) Patent No.: US 6,448,225 B2
(45) Date of Patent: *Sep. 10, 2002

(54) HUMAN GROWTH HORMONE AQUEOUS FORMULATION

(75) Inventors: Barbara H. O'Connor, San Carlos; James Q. Oeswein, Moss Beach, both of CA (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/344,225

(22) Filed: Jun. 25, 1999

Related U.S. Application Data (63) Continuation of application No. 08/891,823, filed on Jul. 14, 1997, now Pat. No. 5,981,485, which is a continuation of application No. 08/117,156, filed as application No. PCT/US93/07149 on Jul. 29, 1993, now Pat. No. 5,763,394, which is a continuation-in-part of application No. 07/923,401, filed on Jul. 31, 1992, now abandoned, which is a continuation-in-part of application No. 07/751,424, filed on Aug. 28, 1991, now abandoned, which is a continuation of application No. 07/182,262, filed on Apr. 15, 1988, now Pat. No. 5,096,885.

(51) Int. Cl.[7] .......................... A61K 38/00; C07K 5/00; C07K 7/00

(52) U.S. Cl. .................. 514/12; 514/2; 514/21

(58) Field of Search .................. 514/12, 2, 21

(56) References Cited

U.S. PATENT DOCUMENTS

| | | | |
|---|---|---|---|
| 3,928,137 A | 12/1975 | Monte et al. | 195/63 |
| 4,100,271 A | 7/1978 | Krezanoski | 514/21 |
| 4,188,373 A | 2/1980 | Krezanoski | 514/21 |
| 4,297,344 A | 10/1981 | Schwinn et al. | 424/101 |
| 4,357,310 A | 11/1982 | Chan et al. | 424/1 |
| 4,474,752 A | 10/1984 | Haslam et al. | 424/78 |
| 4,474,753 A | 10/1984 | Haslam et al. | 424/78 |
| 4,623,717 A | 11/1986 | Fernandes et al. | 530/380 |
| 4,637,834 A | 1/1987 | Thurow | 514/3 |
| 4,783,441 A | 11/1988 | Thurow | 514/3 |
| 4,812,557 A | 3/1989 | Yasushi et al. | 514/2 |
| 4,816,568 A | 3/1989 | Hamilton et al. | 530/399 |
| 4,857,505 A | 8/1989 | Arendt | 514/2 |
| 4,857,506 A | 8/1989 | Tyle | 514/12 |
| 4,917,685 A | 4/1990 | Viswanathan et al. | 514/12 |
| 4,992,419 A | 2/1991 | Woog et al. | 514/8 |
| 5,008,244 A | 4/1991 | Miller et al. | 514/12 |
| 5,096,885 A * | 3/1992 | Pearlman et al. | 514/12 |
| 5,126,324 A | 6/1992 | Clark et al. | 514/12 |
| 5,182,258 A | 1/1993 | Chiou | 514/12 |
| 5,317,012 A | 5/1994 | Kudsk | 514/12 |
| 5,374,620 A | 12/1994 | Clark et al. | 514/12 |
| 5,567,677 A * | 10/1996 | Castensson et al. | 514/12 |
| 5,597,802 A | 1/1997 | Clark et al. | 514/12 |
| 5,763,394 A * | 6/1998 | O'Connor et al. | 514/12 |

FOREIGN PATENT DOCUMENTS

| | | |
|---|---|---|
| AU | 579106 | 1/1985 |
| AU | 8775665 | 1/1988 |
| AU | 8827245 | 6/1989 |
| AU | 30771/89 | 9/1989 |
| AU | 8932756 | 10/1989 |
| AU | 627174 | 11/1989 |
| AU | 8946689 | 7/1990 |
| AU | 611856 | 6/1991 |
| AU | 621327 | 3/1992 |
| AU | 9342783 | 4/1992 |
| AU | 33445/93 | 7/1993 |
| AU | 666007 | 11/1993 |
| AU | 9475668 | 3/1995 |
| AU | 60733/86 | 2/1997 |
| DK | 160459 | 4/1980 |
| DK | 1851/80 | 4/1980 |
| EP | 131864 | 1/1985 |
| EP | 193917 | 9/1986 |
| EP | 211601 | 2/1987 |
| EP | 0 211 601 A2 * | 2/1987 |
| EP | 303746 | 2/1989 |
| EP | 332 222 | 9/1989 |
| EP | 332222 | 9/1989 |
| EP | 374120 | 6/1990 |
| EP | 374 120 | 6/1990 |
| EP | 406856 | 1/1991 |
| EP | 433113 | 6/1991 |
| IL | 72389 | 11/1984 |
| JP | 01-308235 | 12/1989 |
| JP | 08092125 | 4/1996 |
| WO | 89/09614 * | 10/1989 |
| WO | WO 89/09614 | 10/1989 |
| WO | WO 91/14454 | 10/1991 |
| WO | WO 91/15509 | 10/1991 |
| WO | WO 91/18621 | 12/1991 |
| WO | WO 92/08985 | 5/1992 |
| WO | WO 92/17200 | 10/1992 |
| WO | WO 93/00109 | 1/1993 |
| WO | WO 93/12811 | 7/1993 |
| WO | WO 93/19776 | 10/1993 |
| WO | WO 93/22335 | 11/1993 |
| WO | WO 94/03198 | 2/1994 |
| WO | WO 97/39768 | 10/1997 |

OTHER PUBLICATIONS

The Merck Index, 12th ed. S. Budavari editor, Merck and Co.,Inc., Whitehouse Station, N.J. pp 7722 and 8863, 1996.*
Brange, "Galenics of Insulin", Berlin Heidelberg:Springer–Verlag pp. 67–68 (1987).

(List continued on next page.)

Primary Examiner—Christopher S. F. Low
(74) Attorney, Agent, or Firm—Diane L. Marschang (57) ABSTRACT

A stable pharmaceutically acceptable aqueous formulation containing human growth hormone, a buffer, a non-ionic surfactant, and, optionally, a neutral salt, mannitol, or, a preservative, is disclosed. Also disclosed are associated methods for preparing, storing, and using such formulations.

12 Claims, 5 Drawing Sheets-

OTHER PUBLICATIONS

Chawla et al., "Aggregation of Insulin, containing surfactants,in contact with different materials" *Diabetes* 34:420–424 (1985).

Clarke et al., "Method of fomulating IGF–1 with growth hormone" *Journal of Biotechnology Advances* 15(3–4):785.

Dellacha et al., "Physicochemical behaviour and biological activity of bovine growth hormone in acidic solution" *Biochemical Et Biophysica ACTA* 168:95–105 (1968).

Lougheed et al., "Physical Stability of Insulin Formulations" 32:424–432 (1983).

Manning et al., "Stability of Protein Pharmaceuticals" *Pharm. Res.* 6(11):903–918 (1989).

*The Merck Index*, Rahway, NJ:Merck & Co. Inc. pp. 1203, entry No. 7537 (1989).

*The Merck Index*, Rahway, NJ:Merck & Co. Inc. pp. 983, entry No. 7342 (1976).

Pearlman et al. *Current Communications in Molecular Biology*, D. Marshak, D. Liu pp. 23–30 (1989).

*Physician's Desk Reference*, Orawell, NJ:Medical Economics Co. pp. 1049–1050 (1992).

*Physician's Desk Reference*, Orawell, NJ:Medical Economics Co. pp. 1193–1194 (1988).

*Physician's Desk Reference*, Orawell, NJ:Medical Economics Co. pp. 1266–1267 (1992).

Research Disclosure RD370013, "Stabilised protein formulations, particularly, for somatotropin implants–contain stablising polyol, buffer, wetting agent alkali metal halide" (Feb. 10, 1995).

Skottner et al., "Growth responses in a mutant dwarf rat to human growth hormone and recombinant human insulin–like growth factor I" *Endocrinology* 124(5):2519–2526 (1989).

Thurow et al., "Stabilisation of dissolved proteins against denaturation at hydrophobic interfaces" *Diabetologia* 27:212–218 (1984).

Yoshihiro, "Making preparations: Formulations" *Journal Iyakuhin Kenkyu* 20(3):584–586 (1989).

Becker et al., "Chemical, physical, and biological characterization of a dimeric form of biosynthetic human growth hormone" *Biotechnology and Applied Biochemistry* 9:478–487 (1987).

Becker et al., "Isolation and Characterization of a Sulfoxide and a Desamido Derivative of Biosynthetic Human Growth Hormone" *Biotechnol. Appl. Biochem.* (Abstract only) 10:326 (1988).

Currie and Groves, "Protein Stability and Degradation Mechanisms" *Pharmaceutical Biotechnology* pp. 205–214 (1992).

Eckhardt et al., "Effect of freezing on aggregation of human growth hormone" *Pharmaceutical Research* 8(11):1360–1364 (Nov. 1991).

Goddard, "Therapeutic Proteins—A Pharmaceutical Prospective" *Adv. Drug Del. Rev.* 6:103–131 (1991).

*Humatrope (Somatropin [rDNA Origin] for Injection)* (Product Information), Eli Lilly and Company (Feb. 17, 1987).

Kagaya et al., "Pernasal Pharmaceuticals of Human Growth Hormone" *Chem. Abstr.* (Abstract No. 12165x) 113(2):374 (Dec. 29, 1989).

Lewis et al., "Kinetic Study of the Deamidation of Growth Hormone and Prolactin" *Biochem. Biophys. Acta* 214:498–508 (1970).

Oeswein, J.Q. et al., "Aerosolization of Protein Pharmaceuticals" *Proceedings of the Second Respiratory Drug Delivery Symposium*, Dalby, R.N. et al. (eds.), Univ. of Kentucky pp. 14–49 (1991).

Pearlman et al., "Stability and Characterization of Human Growth Hormone" *Stability and Characterization of Protein and Peptide Drugs: Case Histories* pp. 1–57 (1993).

Pikal et al., "Formulation and Stability of Freeze–Dried Proteins: Effects of Moisture and Oxygen on the Stability of Freeze–Dried Formulations of Human Growth Hormone" *DNA and Cell Biology* 74:21–38 (1991).

Pikal et al., "The Effects of Formulation Variables on the Stability of Freeze–Dried Human Growth Hormone" *Pharm. Res.* 8:427–436 (1991).

Timasheff and Arakawa, "Stabilization of proteins structure by solvents" *Protein Structure, A Practical Approach*, T.E. Creighton, IRL Press vol. Chapter 14:331–345 (1989).

"Appendix II: Isosmotic and Isotonic Solutions" *Australian Pharmaceutical Formulary* pp. 521–526.

"Appendix IV: Buffer Solutions" *Australian Pharmaceutical Formulary* pp. 529–533.

Oeswein and Shire, "Physical Biochemistry of Protein Drugs" *Peptide and Protein Drug Delivery*, Lee, ed., New York:Marcel Decker, Inc., Chapter 4, pp. 167–202 (1991).

Yu–Chang et al., "Parenteral Formulations of Proteins and Peptides: Stability and Stabilizers" *Journal of Parenteral Science and Technology* 42(Suppl.):S4–S26 (1988).

\* cited by examiner

HUMAN GROWTH HORMONE AQUEOUS FORMULATION

This application is a continuation application of Ser. No. 08/891,823 filed Jul. 14, 1997, now issued as U.S. Pat. No. 5,981,485, which is a continuation application of Ser. No. 08/117,156 filed Sep. 14, 1993, now issued as U.S. Pat. No. 5,763,394, which is a 371 application of PCT/US93/07149 filed Jul. 29, 1993, which is a continuation-in-part application of Ser. No. 07/923,401 filed Jul. 31, 1992, now abandoned, which is a continuation-in-part application of Ser. No. 07/751,424 filed Aug. 28, 1991, now abandoned, which is a continuation application of Ser. No. 07/182,262 filed Apr. 15, 1988, now issued as U.S. Pat. No. 5,096,885.

FIELD OF THE INVENTION

The present invention is directed to pharmaceutical formulations containing human growth hormone (hGH) and to methods for making and using such formulations. More particularly, this invention relates to such pharmaceutical formulations having increased stability in aqueous formulation.

BACKGROUND OF THE INVENTION

Human growth hormone formulations known in the art are all lyophilized preparations requiring reconstitution. Per vial, Protropin® hGH consists of 5 mg hGH, 40 mg mannitol, 0.1 mg monobasic sodium phosphate, 1.6 mg dibasic sodium phosphate, reconstituted to pH 7.8 (*Physician's Desk Reference,* Medical Economics Co., Orawell, N.J., p. 1049, 1992). Per vial, Humatrope® hGH consists of 5 mg hGH, 25 mg mannitol, 5 mg glycine, 1.13 mg dibasic sodium phosphate, reconstituted to pH 7.5 (*Physician's Desk Reference,* p. 1266, 1992).

For a general review for growth hormone formulations, see Pearlman et al., *Current Communications in Molecular Biology,* eds. D. Marshak and D. Liu, pp. 23–30, Cold Spring Harbor Laboratory Press, Cold Spring Harbor, N.Y., 1989. Other publications of interest regarding stabilization of proteins are as follows.

U.S. Pat. No. 4,297,344 discloses stabilization of coagulation factors II and VIII, antithrombin III, and plasminogen against heat by adding selected amino acids such as glycine, alanine, hydroxyproline, glutamine, and aminobutyric acid, and a carbohydrate such as a monosaccharide, an oligosaccharide, or a sugar alcohol.

U.S. Pat. No. 4,783,441 discloses a method for the prevention of denaturation of proteins such as insulin in aqueous solution at interfaces by the addition of up to 500 ppm surface-active substances comprising a chain of alternating, weakly hydrophilic and weakly hydrophobic zones at pH 6.8–8.0.

U.S. Pat. No. 4,812,557 discloses a method of stabilization of interleukin-2 using human serum albumin.

European Patent Application Publication No. 0 303 746 discloses stabilization of growth promoting hormones with polyols consisting of non-reducing sugars, sugar alcohols, sugar acids, pentaerythritol, lactose, water-soluble dextrans, and Ficoll, amino acids, polymers of amino acids having a charged side group at physiological pH, and choline salts.

European Patent Application Publication No. 0 211 601 discloses the stabilization of growth promoting hormones in a gel matrix formed by a block copolymer containing polyoxyethylene-polyoxypropylene units and having an average molecular weight of about 1,100 to about 40,000.

European Patent Application Publication No. 0 193 917 discloses a biologically active composition for slow release characterized by a water solution of a complex between a protein and a carbohydrate.

Australian Patent Application No. AU-A-30771/89 discloses stabilization of growth hormone using glycine and mannitol.

U.S. Pat. No. 5,096,885 (which is not prior art) discloses a formulation of hGH for lyophilization containing glycine, mannitol, a non-ionic surfactant, and a buffer. The instant invention provides an unexpectedly stabilized aqueous formulation in the absence of glycine.

hGH undergoes several degradative pathways, especially deamidation, aggregation, clipping of the peptide backbone, and oxidation of methionine residues. Many of these reactions can be slowed significantly by removal of water from the protein. However, the development of an aqueous formulation for hGH has the advantages of eliminating reconstitution errors, thereby increasing dosing accuracy, as well as simplifying the use of the product clinically, thereby increasing patient compliance. Thus, it is an objective of this invention to provide an aqueous hGH formulation which provides acceptable control of degradation products, is stable to vigorous agitation (which induces aggregation), and is resistant to microbial contamination (which allows multiple use packaging).

SUMMARY OF THE INVENTION

One aspect of the invention is a stable, pharmaceutically acceptable, aqueous formulation of human growth hormone comprising human growth hormone, a buffer, a non-ionic surfactant, and optionally, a neutral salt, mannitol, and a preservative.

A further aspect of the invention is a method of preventing denaturation of human growth hormone aqueous formulations comprising mixing human growth hormone and a non-ionic surfactant in the range of 0.1–5% (w/v) (weight/volume). In yet another aspect of the invention, this stabilized formulation is stored for 6–18 months at 2–8° C.

DETAILED DESCRIPTION OF THE INVENTION

A. Definitions

The following terms are intended to have the indicated meanings denoted below as used in the specification and claims.

The terms "human growth hormone" or "hGH" denote human growth hormone produced by methods including natural source extraction and purification, and by recombinant cell culture systems. Its sequence and characteristics are set forth, for example, in *Hormone Drugs,* Gueriguian et al., U.S.P. Convention, Rockville, Md. (1982). The terms likewise cover biologically active human growth hormone equivalents, e.g., differing in one or more amino acid(s) in the overall sequence. Furthermore, the terms used in this application are intended to cover substitution, deletion and insertion amino acid variants of hGH, or posttranslational modifications. Two species of note are the 191 amino acid native species (somatropin) and the 192 amino acid N-terminal methionine (met) species (somatrem) commonly obtained recombinantly.

The term "pharmaceutically effective amount" of hGH refers to that amount that provides therapeutic effect in an administration regimen. The compositions hereof are prepared containing amounts of hGH at least about 0.1 mg/ml, upwards of about 10 mg/ml, preferably from about 1 mg/ml to about 20 mg/ml, more preferably from about 1 mg/ml to about 5 mg/ml. For use of these compositions in administration to human patients suffering from hypopituitary dwarfism, for example, these compositions contain from about 0.1 mg/ml to about 10 mg/ml, corresponding to the currently contemplated dosage regimen for the intended treatment. The concentration range is not critical to the invention, and may be varied by the clinician.

B. General Methods

The instant invention has no requirement for glycine. Glycine is an optional component of the aqueous formulation, although with less advantage in the aqueous formulations hereof compared with those formulations that are lyophilized for later reconstitution. Amounts of glycine will range from 0 mg/ml to about 7 mg/ml.

Non-ionic surfactants include a polysorbate, such as polysorbate 20 or 80, etc., and the poloxamers, such as poloxamer 184 or 188, Pluronic® polyols, and other ethylene/polypropylene block polymers, etc. Amounts effective to provide a stable, aqueous formulation will be used, usually in the range of from about 0.1% (w/v) to about 5% (w/v), more preferably, 0.1% (w/v) to about 1% (w/v). The use of non-ionic surfactants permits the formulation to be exposed to shear and surface stresses without causing denaturation of the protein. For example, such surfactant-containing formulations are employed in aerosol devices such as those used in pulmonary dosing and needleless jet injector guns.

Buffers include phosphate, Tris, citrate, succinate, acetate, or histidine buffers. Most advantageously, the buffer is in the range of about 2 mM to about 50 mM. The preferred buffer is a sodium citrate buffer.

A preservative is included in the formulation to retard microbial growth and thereby allow "multiple use" packaging of the hGH. Preservatives include phenol, benzyl alcohol, meta-cresol, methyl paraben, propyl paraben, benzalconium chloride, and benzethonium chloride. The preferred preservatives include 0.2–0.4% (w/v) phenol and 0.7–1% (w/v) benzyl alcohol.

Suitable pH ranges, adjusted with buffer, for aqueous hGH formulation are from about 4 to 8, more preferably about 5.5 to about 7, most advantageously 6.0. Preferably, a buffer concentration range is chosen to minimize deamidation, aggregation, and precipitation of hGH.

Mannitol may optionally be included in the aqueous hGH formulation. The preferred amount of mannitol is about 5 mg/ml to about 50 mg/ml. As an alternative to mannitol, other sugars or sugar alcohols are used, such as lactose, trehalose, stachiose, sorbitol, xylitol, ribitol, myoinositol, galactitol, and the like.

Neutral salts such as sodium chloride or potassium chloride are optionally used in place of sugars or sugar alcohols. The salt concentration is adjusted to near isotonicity, depending on the other ingredients present in the formulation. For example, the concentration range of NaCl may be 50–200 mM, depending on the other ingredients present.

In a preferred embodiment, the formulation of the subject invention comprises the following components at pH 6.0.

| Ingredient | Quantity (mg/ml) |
|---|---|
| hGH | 5 |
| Sodium Chloride | 8.8 |
| Polysorbate 20 | 2.0 |
| Sodium citrates | 2.5 |
| Phenol | 2.5 |
| Sterile water | 1 ml |

It will be understood that the above quantities are somewhat flexible within ranges, as set forth in more detail above, and that the materials are interchangeable within the component categories. That is, polysorbate 80, or a poloxamer, may be substituted for polysorbate 20, a succinate or acetate buffer could instead be employed, and alternative preservatives and different pHs could be used. In addition, more than one buffering agent, preservative, sugar, neutral salt, or non-ionic surfactant may be used. Preferably, the formulation is isotonic and sterile.

In general, the formulations of the subject invention may contain other components in amounts not detracting from the preparation of stable forms and in amounts suitable for effective, safe pharmaceutical administration. For example, other pharmaceutically acceptable excipients well known to those skilled in the art may form a part of the subject compositions. These include, for example, various bulking agents, additional buffering agents, chelating agents, antioxidants, cosolvents and the like; specific examples of these could include trimethylamine salts ("Tris buffer"), and disodium edetate.

EXPERIMENTAL EXAMPLES

A. Assay Methods

Anion exchange chromatography (HPIEC) was run on a TSK DEAE 5PW column (1.0×7.5 cm) at 45° C. with a flow rate of 0.5 ml/min. The column was equilibrated in 50 mM potassium phosphate, pH 5.5, containing 10% (w/v) acetonitrile. Elution was performed using a 25 minute gradient from 50–100 mM potassium phosphate, pH 5.5 with constant 10%(w/v) acetonitrile. The column load was 83 $\mu$g of protein. Detection was at 230 nM.

Nondenaturing size exclusion chromatography was run on a TSK 2000 SWXL column in 50 mM sodium phosphate, pH 7.2 containing 150 mM sodium chloride. The flow rate was 1 ml/min, with a 50–75 $\mu$g column load and detection at either 214 and 280 nm.

Denaturing size exclusion chromatography was run on a Zorbax GF250 column in 200 mM sodium phosphate, pH 6.8–7.2/0.1% SDS. The flow rate was 1.0 ml/minute, with a with a 50–75 $\mu$g column load and detection at either 214 and 280 nm.

B. Formulation Preparation

In general, aqueous hGH formulation samples for analysis in these experimental examples were prepared by buffer exchange on a gel filtration column. The elution buffer contained either sodium chloride or mannitol, buffer and the non-ionic surfactant in their final ratios. This resulting solution was diluted to a desired hGH concentration and the preservative was added. The solution was sterile filtered using a sterilized membrane filter (0.2 micron pore size or equivalent) and filled into sterile 3 cc type 1 glass vials, stoppered and sealed with aqueous-type butyl rubber stoppers and aluminum flip-off type caps.

The aqueous hGH formulation used in the experimental examples consisted of 5.0 mg somatropin (Genentech, Inc.), 45.0 mg mannitol, 2.5 mg phenol, 2.0 mg polysorbate 20, and 2.5 mg sodium citrate, pH 6.0, per ml of solution. The lyophilized formulation used as a reference for comparison in the examples consisted of 5.0 mg somatropin, 1.7 mg glycine, 45.0 mg mannitol, 1.7 mg sodium phosphate, 9 mg benzyl alcohol per ml sterile solution after reconstitution.

C. Example I

Chemical Stability of the Aqueous Formulation

Vials of the hGH aqueous formulation (lots 12738/55-102 and 12738/55-105) were incubated at either recommended storage temperatures of 2–8° C., or elevated storage temperatures of 15° C., or 25° C., and then removed at various time points and assayed for changes in pH, color and appearance, and protein concentration. In addition, samples were incubated at 40° C. in order to study degradation patterns under extreme stress conditions. Degradation patterns for the aqueous formulation were also compared to the known degradation patterns for lyophilized growth hormone.

Figure 1:
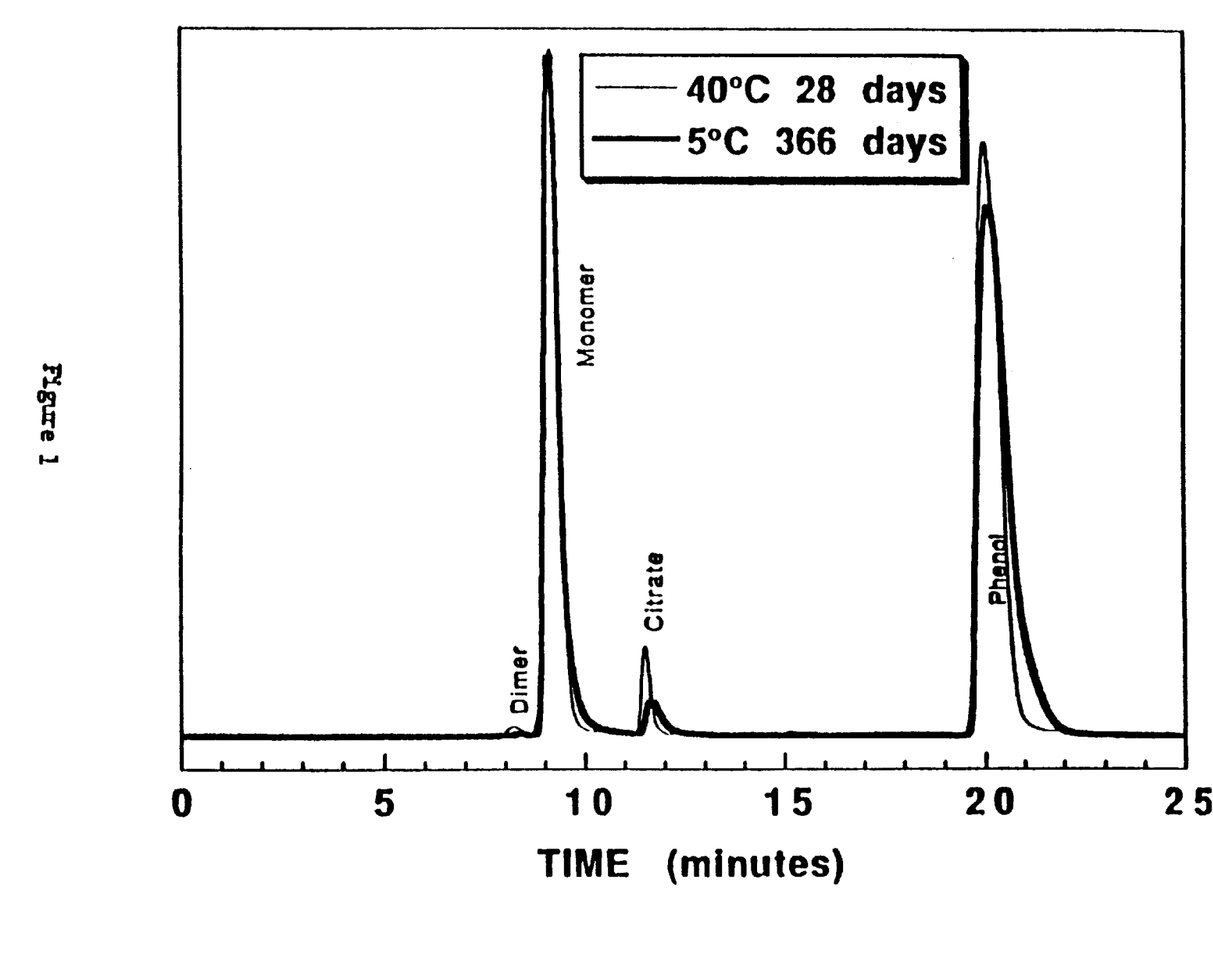
FIG. 1 is a size exclusion chromatogram of aqueous growth hormone formulation stored for 28 days at 40° C. (i.e., thermally stressed) and for one year at 5° C. (i.e., recommended conditions for storage).

After storage at 2–8° C. for up to one year, the aqueous formulation showed insignificant changes in pH,, color and appearance, and protein concentration. Nondenaturing size exclusion HPLC performed on samples stored for up to one year at 2–8° C. showed no significant aggregation of the drug product (FIG. 1). This result is unexpected in light of the teaching of U.S. Pat. No. 5,096,885 that glycine contributes to preventing aggregation in the lyophilized preparation.

At temperatures above 8° C., little or no changes in pH or protein concentration were observed over time. Visual inspection revealed an increase in opalescence with time for samples stored at 40° C. This change was minimal during storage at 15–25° C. and has not been observed during 2–8° C. storage.

Figure 2:
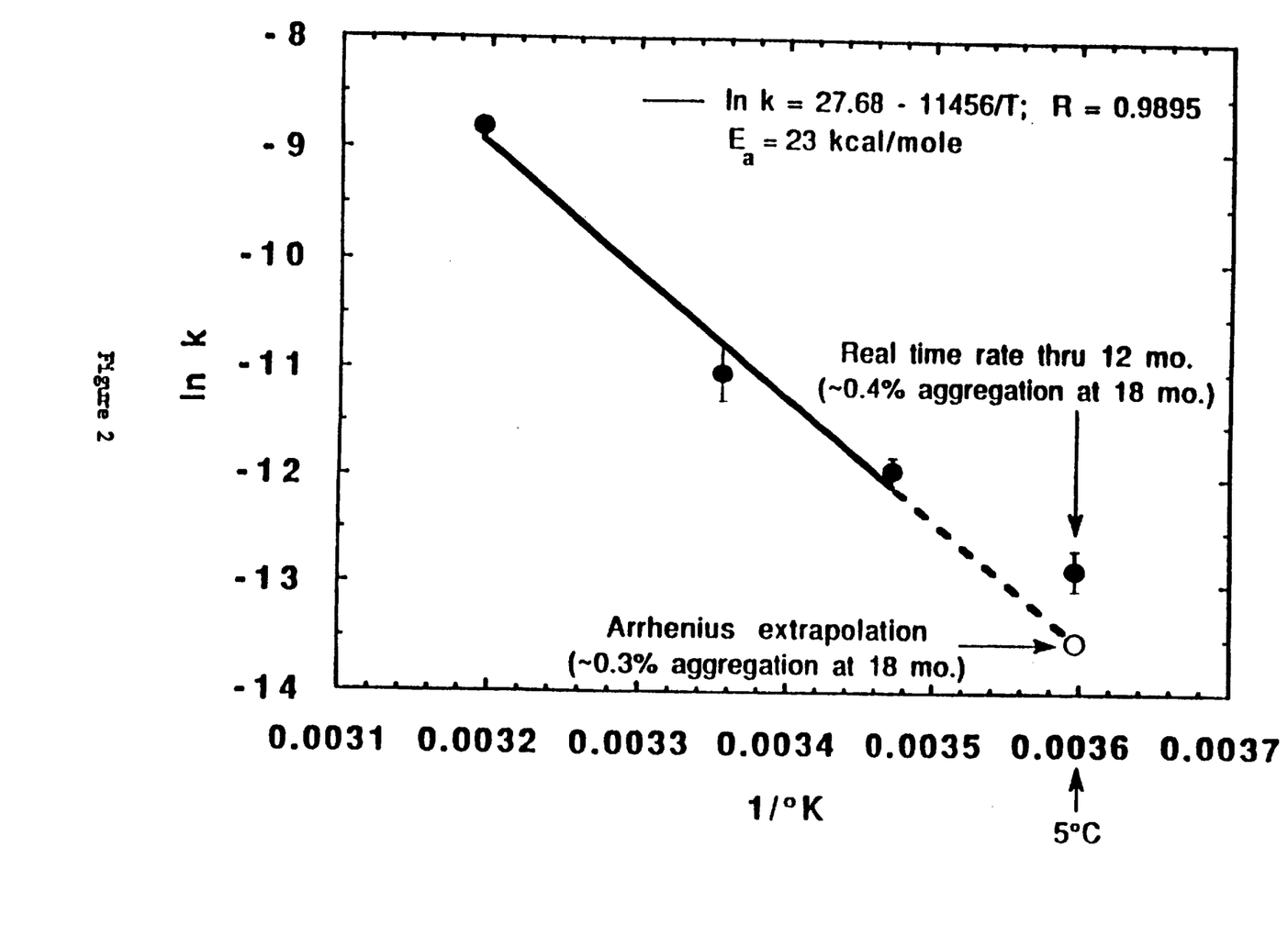
FIG. 2 is a plot of Arrhenius rate analysis of growth hormone aggregation in aqueous formulation.

The amount of degradation product was calculated as an area percentage of the total hGH area of the chromatogram. The rate constant for each reaction was then calculated by subtracting the percentage of degradation product from 100%, taking the $\log_{10}$, and plotting against the time in days. The slope of a straight line to fit these data was used as the reaction constant (k). Arrhenius analysis was done by plotting the natural logarithm (ln) of the absolute value of each calculated reaction rate constant at 15, 25, and 40° C. as a function of the inverse absolute temperature and then extrapolating to 5° C. Arrhenius and real time rate analysis (FIG. 2) of data from the size exclusion HPLC indicate that the amount of growth hormone aggregation after 18 months of storage will be less than 1% (w/v).

Figure 3:
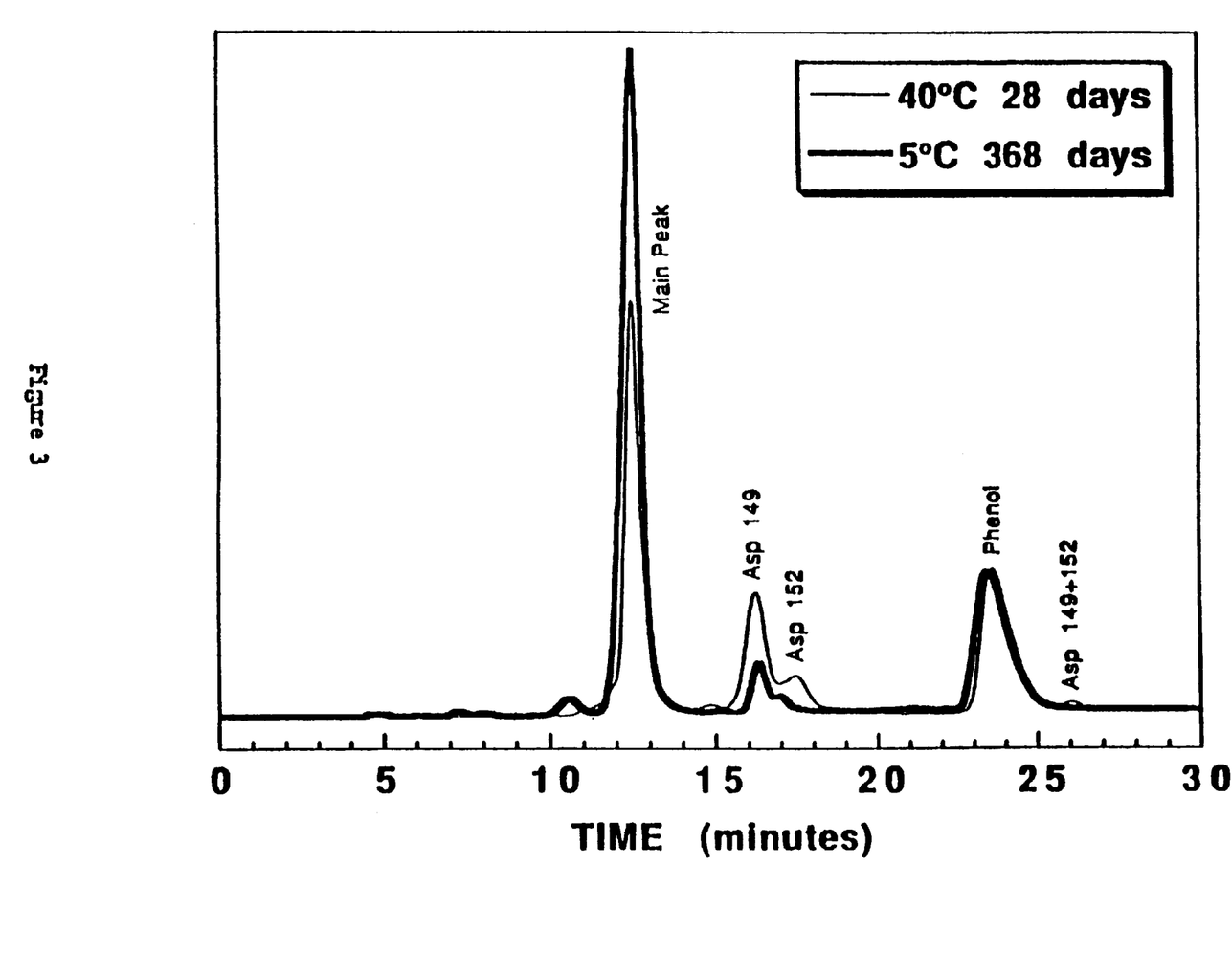
FIG. 3 is an anion exchange chromatogram comparing a thermally stressed (40° C.) aqueous formulation hGH sample with an aqueous formulation hGH sample stored under recommended conditions (2–8° C.) for one year.
Figure 4:
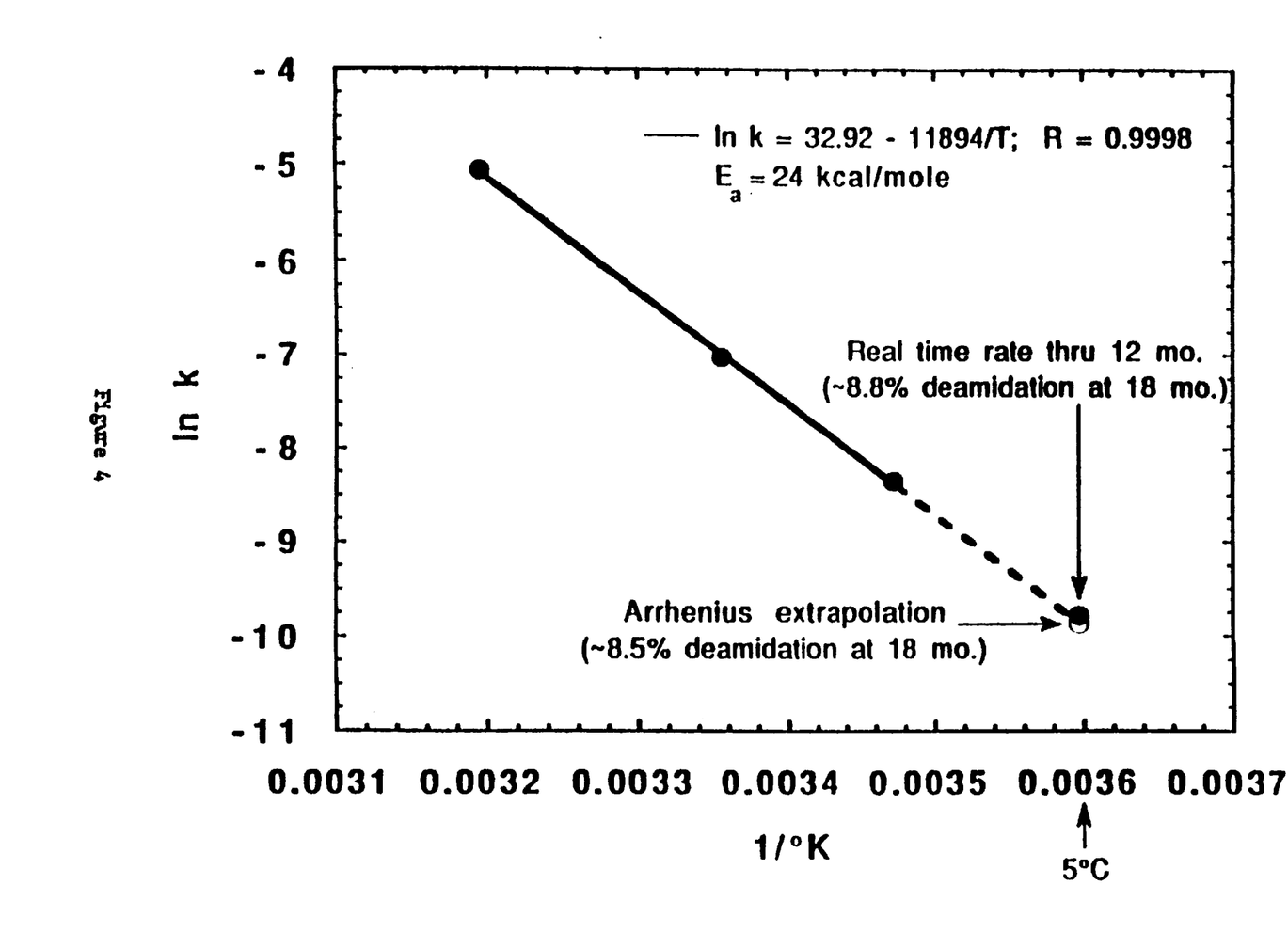
FIG. 4 is a plot of Arrhenius rate analysis of hGH deamidation in aqueous formulation.

Anion exchange HPLC analysis performed on the aqueous hGH formulation stored at 40° C. indicated an increase in acidic peaks over 28 days (FIG. 3). Three of these peaks, eluting at about 16, 17.5, and 26 minutes, were produced by hGH deamidation at positions 149, 152, and 149 plus 152. Arrhenius and real time rate analysis (FIG. 4) of data from this method, were plotted as described above, and indicate that the amount of deamidated hGH in these lots after 18 months of storage at 2–8° C. will be about 9% (w/v). This includes an initial amount of about 2.4% (w/v) deamidated hGH at time zero. Values as high as 15% (w/v) deamidation have been reported for other hGH products (Larhammar, H., et al., (1985) *Int. J. Pharmaceutics* 23:13–23). Although the rate of deamidation is faster in the aqueous state, this rate is minimized at pH 6.0 and below.

D. Example II

Physical Stability of the Aqueous Formulation

Each of six vials of lyophilized growth hormone were reconstituted with 1 ml bacteriostatic water for injection (BWFI) U.S.P. After dissolving, the contents were transferred to 3 cc vials, stoppered, and capped to provide the same configuration as that for the aqueous formulation. The six vials of the hGH aqueous formulation and six vials of reconstituted lyophilized hGH were vigorously shaken top to bottom in a horizontal fashion on a Glas-Col Shaker-in-the-Round at 240 jolts per minute using a stroke setting of 2.5, giving a horizontal displacement of 8±1 cm for up to 24 hours at room temperature to assess the effects of agitation on physical stability of the hGH aqueous formulation. All twelve samples were placed in a straight line on the shaker to assure that they were all exposed to the same force for each formulation. Two vials were removed for assays at 30 minutes, 6 hours, and 24 hours.

The results are displayed in Table I. Agitation produced very little change in the visual clarity of the aqueous formulation. There was no change in the content of total growth hormone monomer as detected by a nondenaturing size exclusion HPLC assay. This assay detects noncovalent aggregates, which are completely dispersed by SDS in a denaturing size exclusion HPLC assay.

By comparison, these results also demonstrated that the reconstituted lyophilized product was more sensitive to treatment, even after only 30 minutes of shaking. This sensitivity is typical for all currently available formulations of hGH, other than the aqueous formulation of the instant invention. The inclusion of the non-ionic surfactant is the most important factor in preventing this phenomenon from occurring.

TABLE I

Effects of Agitation at Room Temperature on hGH Aqueous Formulation vs. Reconstituted Lyophilized Formulation

| Sample | Color/Appearance | % HPSEC Monomer | % Soluble Protein | % Total[1] Monomer |
|---|---|---|---|---|
| Unshaken | | | | |
| Aqueous | clear/colorless | 99.7 | ND | ND |
| Aqueous | clear/colorless | 99.9 | ND | ND |
| Lyophilized | clear/colorless | 99.0 | 100 | 99.0 |
| Lyophilized | clear/colorless | ND | ND | ND |
| Shaken 0.5 hr | | | | |
| Aqueous | very slightly opalescent/colorless | 99.9 | 100 | 99.9 |

TABLE I-continued

Effects of Agitation at Room Temperature on hGH Aqueous Formulation vs. Reconstituted Lyophilized Formulation

| Sample | Color/Appearance | % HPSEC Monomer | % Soluble Protein | % Total[1] Monomer |
|---|---|---|---|---|
| Aqueous | very slightly opalescent/colorless | 100.0 | 100 | 100.0 |
| Lyophilized | slightly opalescent/colorless | 93.6 | 100 | 93.6 |
| Lyophilized | clear/colorless | 92.8 | 100 | 92.8 |
| Shaken 6 hr | | | | |
| Aqueous | slightly opalescent/colorless | 99.9 | 100 | 99.9 |
| Aqueous | opalescent/colorless | 99.8 | 100 | 99.8 |
| Lyophilized | very opalescent/yellow to brown | 80.5 | 73 | 58.8 |
| Lyophilized | very opalescent/yellow to brown | 72.7 | 61.7 | 44.9 |
| Shaken 24 hr | | | | |
| Aqueous | slightly opalescent/colorless | 99.8 | 100 | 99.8 |
| Aqueous | clear/colorless | 99.8 | ND | ND |
| Lyophilized | very cloudy/yellow to brown | 60.6 | 21.5 | 13.0 |
| Lyophilized | very cloudy/yellow to brown | 56.7 | 14.8 | 8.4 |

[1]Total monomer = (% monomer × % soluble protein)/100

E. Example III

Preservative Effectiveness in the Aqueous Formulation

Samples of hGH aqueous formulation were subjected to bacterial challenge according to an abbreviated challenge using the standard U.S.P. test. In this test, a suspension of either *E. coli* or *S. aureus* was added to an aliquot of hGH aqueous formulation to give a final concentration of bacteria between $10^5$ to $10^6$ CFU/ml. Viable bacteria remaining in the tubes were counted immediately and after 4 and 24 hours incubation at 20–25° C. The percentage change in the concentration of the microorganisms during the challenge was calculated according to the following equation:

$$\% \text{ initial titer} = \frac{\text{titer at } T = X \text{ hours} \times 100}{\text{titer at } T = 0}$$

The results of this experiment indicated that for two species of bacteria, concentrations of viable bacteria were reduced to less than 0.01% of the initial concentrations after 24 hours.

F. Example IV

Substitution of Mannitol with Salt

Figure 5:
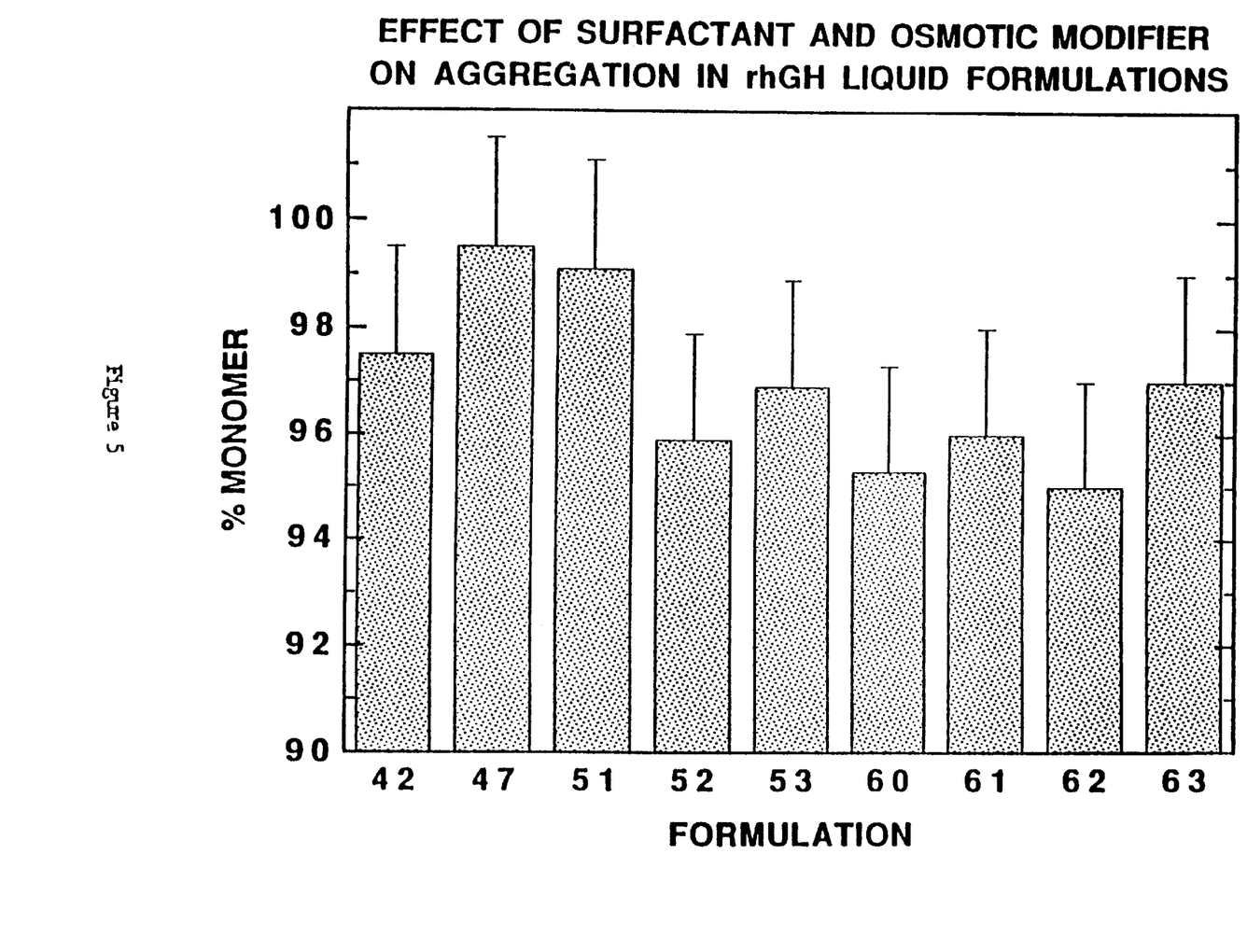
FIG. 5 is a graph of the percentage monomer present in the various formulations where mannitol has been substituted with a neutral salt.

In this experiment aqueous formulations of hGH were compared that varied in concentrations of salt, mannitol, and non-ionic surfactant. All formulations contained 5 mg/ml hGH/ 0.25% (w/v) phenol/ 10 mM sodium citrate, pH 6.0. Samples were stored 3–4 months at 2–8° C. FIG. 5 indicates the percentage monomer present in the indicated formulations. The Table below indicates the composition of each formulation. These results demonstrate the unexpected stability of hGH in a formulation in which mannitol has been substituted with a neutral salt in the presence of a surfactant.

TABLE 3

Formulations Tested in FIG. 5

| Formulation # | Composition |
|---|---|
| 42 | 0.1% (w/v) polysorbate 20 50 mM mannitol |
| 47 | 0.1% (w/v) poloxamer/188 0.1M NaCl |
| 51 | 0.5% (w/v) polysorbate 20 50 mM mannitol |
| 52 | 0.1% (w/v) poloxamer 188 50 mM mannitol |
| 53 | 0.1% (w/v) poloxamer 184 50 mM mannitol |
| 60 | 0.2% (w/v) polysorbate 20 0.1M NaCl |
| 61 | 0.2% (w/v) polysorbate 20 0.05M NaCl |
| 62 | 0.2% (w/v) polysorbate 20 0.15M NaCl |
| 63 | 0.2% (w/v) polysorbate 20 50 mM mannitol |

We claim:

1. A stable aqueous formulation of human growth hormone comprising:
   a) 1 mg/ml to 20 mg/ml human growth hormone;
   b) buffer providing pH 5.5 to pH 7;
   c) 0.1% w/v to 1 % w/v nonionic surfactant; and
   d) mannitol;
   wherein said aqueous formulation is free of glycine and is stable upon storage for 6 to 18 months at 2 to 8° C.

2. The formulation of claim 1 further comprising a preservative.

3. The formulation of claim 2 wherein said preservative is selected from the group consisting of phenol, benzyl alcohol, meta-cresol, methyl paraben, propyl paraben, benzalkonium chloride, and benzethonium chloride.

4. The formulation of claim 3 wherein said preservative is phenol.

5. The formulation of claim 3 wherein the concentration of phenol in the formulation is 0.2% (w/v) to 0.4% (w/v).

6. The formulation of claim 1 which further comprises neutral salt.

7. The formulation of claim 1 wherein the concentration of mannitol in said formulation is 5 mg/ml to 50 mg/ml.

8. The formulation of claim 1 wherein said buffer is selected from the group consisting of citrate, phosphate, Tris, succinate, and histidine buffers.

9. The formulation of claim 8 wherein said buffer is citrate buffer.

10. The formulation of claim 8 wherein said buffer is histidine buffer.

11. The formulation of claim 1 wherein the non-ionic surfactant is poloxamer or polysorbate.

12. A method of making a storage stable aqueous formulation of human growth hormone comprising mixing said human growth hormone and an aqueous, pharmaceutically acceptable vehicle which includes
   a) said human growth hormone at a concentration of 1 mg/ml to 20 mg/ml;
   b) buffer providing pH 5.5 to pH 7;
   c) 0.1% w/v to 1% w/v nonionic surfactant; and
   d) mannitol;
   wherein said aqueous formulation is free of glycine and is stable upon storage for 6 to 18 months at 2 to 8° C.

* * * * *

UNITED STATES PATENT AND TRADEMARK OFFICE
CERTIFICATE OF CORRECTION

PATENT NO.      : 6,448,225 B2
DATED           : September 10, 2002
INVENTOR(S)     : O'Connor et al.

It is certified that error appears in the above-identified patent and that said Letters Patent is hereby corrected as shown below:

<u>Column 8,</u>
Line 40, delete "claim 3" and insert therefor -- claim 4 --.

Signed and Sealed this

Twenty-second Day of April, 2003

JAMES E. ROGAN
*Director of the United States Patent and Trademark Office*